(12) United States Patent
Oh et al.

(10) Patent No.: US 8,737,667 B2
(45) Date of Patent: May 27, 2014

(54) EARPHONE DEVICE HAVING BIOLOGICAL INFORMATION MEASURING APPARATUS

(75) Inventors: Jung-Taek Oh, Seoul (KR); Min-Hyoung Lee, Yongin-si (KR)

(73) Assignee: Samsung Electronics Co., Ltd (KR)

( * ) Notice: Subject to any disclaimer, the term of this patent is extended or adjusted under 35 U.S.C. 154(b) by 556 days.

(21) Appl. No.: 12/900,130

(22) Filed: Oct. 7, 2010

(65) Prior Publication Data

US 2011/0081037 A1    Apr. 7, 2011

(30) Foreign Application Priority Data

Oct. 7, 2009    (KR) .......................... 10-2009-0095161

(51) Int. Cl.
*H04R 25/00*    (2006.01)

(52) U.S. Cl.
USPC ........... 381/376; 381/367; 381/370; 381/384; 600/309; 379/430

(58) Field of Classification Search
USPC ................. 381/367, 376, 370, 384; 600/309; 379/430
See application file for complete search history.

(56) References Cited

U.S. PATENT DOCUMENTS

| | | | |
|---|---|---|---|
| 5,210,792 A * | 5/1993 | Kajihara | 379/430 |
| 5,369,857 A * | 12/1994 | Sacherman et al. | 29/594 |
| 7,209,775 B2 | 4/2007 | Bae et al. | |
| 2002/0131616 A1 * | 9/2002 | Bronnikov et al. | 381/370 |
| 2006/0160582 A1 * | 7/2006 | Jeun et al. | 455/575.1 |
| 2008/0013777 A1 * | 1/2008 | Park et al. | 381/384 |
| 2008/0132798 A1 * | 6/2008 | Hong et al. | 600/508 |
| 2010/0152556 A1 | 6/2010 | Oh | |

FOREIGN PATENT DOCUMENTS

| | | |
|---|---|---|
| KR | 1020060007334 | 1/2006 |
| KR | 100786279 | 12/2007 |
| KR | 1020080056950 | 6/2008 |
| KR | 20-0443339 | 2/2009 |
| KR | 1020100068940 | 6/2010 |

OTHER PUBLICATIONS

Yamaha, BodiBeat BF-1 Owner's Manual, 2009.

* cited by examiner

*Primary Examiner* — Davetta W Goins
*Assistant Examiner* — Amir Etesam
(74) *Attorney, Agent, or Firm* — The Farrell Law Firm, P.C.

(57) ABSTRACT

An earphone device having a biological information measuring apparatus, structured to facilitate insertion into a user's ear or to absorb vibration generated by external movement before or after the insertion. To this end, the earphone device includes a speaker portion, a sensor housing rotatably coupled with the speaker portion, a shaft provided in the speaker portion and the sensor housing to couple the speaker portion with the sensor housing such that the speaker portion and the sensor housing rotate together, a support housing coupled with the shaft to pass the shaft therethrough, the support housing supporting rotation of the speaker portion and the sensor housing, and a stopper portion provided in the shaft and the support housing to rotate the speaker portion and the sensor housing and then stop them before or after insertion into a user's ear, thereby facilitating the insertion or urging the speaker portion to contact the user's ear.

16 Claims, 28 Drawing Sheets

EARPHONE DEVICE HAVING BIOLOGICAL INFORMATION MEASURING APPARATUS

PRIORITY

This application claims priority under 35 U.S.C. §119(a) to a Korean Patent Application filed in the Korean Intellectual Property Office on Oct. 7, 2009 and assigned Serial No. 10-2009-0095161, the entire disclosure of which is incorporated herein by reference.

BACKGROUND OF THE INVENTION

1. Field of the Invention

The present invention relates to an earphone device having a biological information (or living body information) measuring apparatus structured to facilitate insertion of an earphone into a user's ear and to absorb vibration generated by external artificial movement before and after insertion of the earphone.

2. Description of the Related Art

Generally, a biological information measuring apparatus measures biological information about the bloodstream of a human body, such as pulse, heart rate, and the like. Products embodying these devices have various shapes and sizes, and some of them have been miniaturized to be portable or integrally incorporated within other products.

For example, there is a device having a pulse sensor embedded in a wrist watch. As the user contacts the pulse sensor provided in the wrist watch with a finger tip, a pulse is optically detected by the pulse sensor and a pulse rate is displayed on a display unit of a main body of the wrist watch.

Such a conventional biological information measuring apparatus generally uses an electrocardiogram (ECG) sensor, which measures a pulse rate by detecting an ECG signal with a multi-polar electrode. Also introduced is an optical sensor which measures biological information by radiating light onto a skin surface of a human body using a light emitting diode (LED) and detecting light output from the skin surface by the action of scattering in the human body using a photo diode (PD).

As disclosed in International Publication No. WO 2005/034742, which is incorporated herein by reference, the conventional biological information measuring apparatus is structured such that a pulse measuring sensor, one of transmissive optical sensors, for a part of a human ear known as the tragus is in the shape of a nipper and thus presses the tragus. Like a general nipper, the pulse-measuring sensor also includes two arms, a pivot, and a spring.

Recently, research is being conducted to downsize biological information measuring apparatuses, and as part of this, a device for mounting the measuring apparatus using the biological structure of a user's ears has been developed.

A biological information measuring apparatus connected to an earphone may operate according to the following schemes: measuring biological information through the skin in a transmissive manner by binding the measuring apparatus in a lobe by means of an additional apparatus independently of the earphone; measuring biological information through the skin in a transmissive manner by binding the measuring apparatus in an auricle by means of an apparatus independent of the earphone; measuring biological information through the skin in a transmissive manner by binding the measuring apparatus in a tragus portion; and especially for a wireless earphone, measuring biological information in a contact portion between the wireless earphone and skin except for an ear portion in a refractive manner.

However, the foregoing conventional schemes may have some problems. That is, if a sensor unit is completely separated from an earphone structure, a user may need an additional wire-connected device and do the troublesome work of mounting the sensor unit after inserting the earphone into the ear.

To solve the above-described problems, the sensor unit may be integrated into the earphone. In this case, however, the user may feel discomfort during or after wearing the sensor unit and measurement may be totally impossible due to significant signal distortion caused by artificial movement generated during times when the user is moving, such as during exercise.

As such, when the biological information measuring apparatus is mounted in the earphone, it performs measurements on the user's auricle portion in the transmissive manner, whereby much noise may be generated by the movement of the earphone and the head portion. Generally there is no way to prevent the movement of the earphone and the head portion due to the existence of only an ear hook portion to secure the earphone to the user's ear.

As shown in FIG. 1, a neckband type earphone 1 in a shape similar to a headphone where speakers are mounted on both ends of a neckband behind the head of a user has been developed in an effort to solve the foregoing problems.

The neckband type earphone 1 includes a neckband portion 2, sub neckband portions 3 provided at both ends of the neckband portion 2, and speaker portions 4 provided on the sub neckband portions 3. The neckband portion 1 includes a battery unit 5, a sensor controller 6, and a radio frequency (RF) unit 7.

The neckband type earphone 1 also includes a biological information measuring apparatus, which includes a sensor unit 8 having an LED 8a and a PD 8b.

However, as shown in FIG. 2, the conventional neckband type earphone 1 is hung on a tragus portion 101 of a user's ear 100, and thus the speaker portions 4 cannot be completely inserted.

To address this problem, a high-elasticity wire, which is easily deformed, is inserted into the sub-neckband portions of a conventional neckband type earphone, such that they are freely deformed during insertion of the earphone into a user's ear. However, when the user having worn the earphone strenuously exercises, for example, runs or walks, the wire is likely to be deformed by shock and vibration perpendicular to the user's moving direction. As a result, the earphone is separated from the user's ear and thus the biological information measuring apparatus cannot measure the user's biological information. Moreover, after the earphone is used for a long time, the sub-neckband portions are prone to damage.

To extract a biological signal, a sensor unit is generally positioned in a body contact portion, which may be a tragus, an entry to an internal auditory canal, or a temple, which contacts a speaker portion. However, near the temple, the user's hair and hair follicles as well as skin are present, resulting in a limitation in biological signal extraction using light.

If measurement is performed in the tragus, or through entry to the internal auditory canal of the user's ear, the earphone may not be easily inserted due to the size of the speaker portion having the sensor unit mounted thereon, in spite of removal of the influence of hair or the like.

Accordingly, there is a need for an apparatus which facilitates insertion of an earphone into a user's ear by using rotation, and delivers only a minimal part of a shock and vibration to the earphone, caused by strenuous movement after insertion of the earphone, by absorbing the shock and vibration, thereby guaranteeing convenience in wearing a biological information measuring apparatus and improving the performance of the biological information measuring apparatus.

SUMMARY OF THE INVENTION

An aspect of the present invention is to address at least the above problems and/or disadvantages and to provide at least the advantages described herein. Accordingly, an aspect of the present invention is to provide an earphone device having a biological information measuring apparatus, which is structured with at least a shaft, a support housing, and a stopper portion to facilitate insertion of an earphone into a user's ear, thereby improving the comfort of a product and thus reducing discomfort after wearing the earphone, and preventing signal distortion from occurring due to vibrations generated during the user's strenuous exercise.

Moreover, another aspect of the present invention is to provide an earphone device having a biological information measuring apparatus, which is structured with at least a gear portion and a support housing to facilitate insertion of an earphone into a user's ear, thereby improving the comfort of a product and thus reducing discomfort while wearing the earphone, and preventing signal distortion from occurring due to vibrations generated during the user's strenuous exercise.

Furthermore, another aspect of the present invention is to provide an earphone device having a biological information measuring apparatus, which is structured with an elastic portion for reducing vibration by absorbing inertial forces generated by external movement after insertion of an earphone, and increasing or reducing stiffness in a direction affecting the comfort of a product, thereby preventing signal distortion from occurring due to vibrations generated during the user's strenuous exercise.

According to an aspect of the present invention, there is provided an earphone device including a biological information measuring apparatus, the earphone device including a speaker portion, a sensor housing rotatably coupled with the speaker portion, a shaft provided in the speaker portion and the sensor housing to couple the speaker portion with the sensor housing such that the speaker portion and the sensor housing rotate together, a support housing coupled with the shaft to pass the shaft therethrough, the support housing supporting rotation of the speaker portion and the sensor housing, and a stopper portion provided in the shaft and the support housing to rotate the speaker portion and the sensor housing and then stop them before or after insertion into a user's ear, thereby facilitating the insertion or urging the speaker portion to contact the user's ear.

According to another aspect of the present invention, there is provided an earphone device including a biological information measuring apparatus, the earphone device including a speaker portion, a sensor housing rotatably coupled with the speaker portion, a shaft provided in the speaker portion and the sensor housing to couple the speaker portion with the sensor housing such that the speaker portion and the sensor housing rotate together, a support housing coupled with the shaft to pass the shaft therethrough, the support housing supporting rotation of the speaker portion and the sensor housing, a stopper portion provided in the shaft and the support housing to rotate the speaker portion and the sensor housing and then stop them before or after insertion into a user's ear, thereby facilitating the insertion or urging the speaker portion to contact the user's ear, and an elastic portion provided in the support housing to absorb inertial forces generated by external movement.

According to another aspect of the present invention, there is provided an earphone device including a biological information measuring apparatus, the earphone device including a speaker portion, a sensor housing rotatably coupled with the speaker portion, a gear portion provided in the speaker portion and the sensor housing to rotate the sensor housing about a first rotation axis and the speaker portion about a second rotation axis, and a support housing for supporting the speaker portion and the sensor housing such that the speaker portion and the sensor housing rotate about the second rotation axis and the first rotation axis by means of the gear portion.

According to another aspect of the present invention, there is provided an earphone device including a biological information measuring apparatus, the earphone device including a speaker portion, a sensor housing rotatably coupled with the speaker portion, a gear portion provided in the speaker portion and the sensor housing to rotate the sensor housing about a first rotation axis and the speaker portion about a second rotation axis, a support housing for supporting the speaker portion and the sensor housing to allow the speaker portion and the sensor housing to rotate about the second rotation axis and the first rotation axis by means of the gear portion, and an elastic portion provided in the support housing to absorb inertial forces generated by external movement.

BRIEF DESCRIPTION OF THE DRAWINGS

The above and other features and advantages of exemplary embodiments of the present invention will be more apparent from the following detailed description taken in conjunction with the accompanying drawings, in which.

DETAILED DESCRIPTION OF EMBODIMENTS OF THE PRESENT INVENTION

Figure 1:
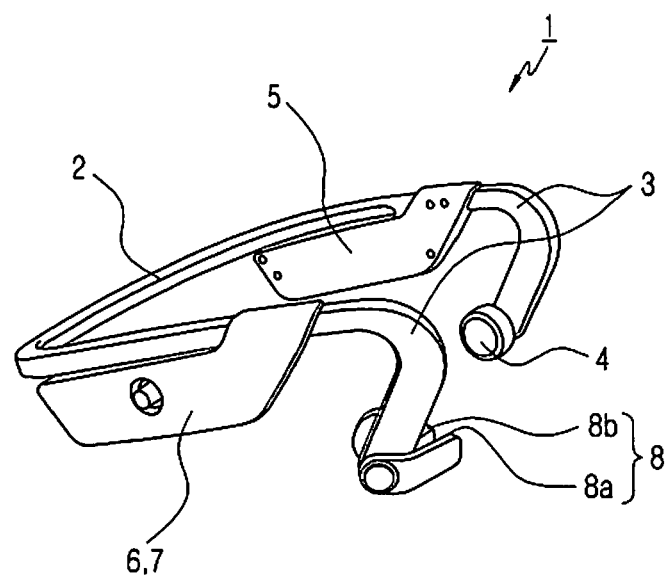
FIG. 1 is a perspective view of an earphone device having a biological information measuring apparatus according to the prior art.
Figure 2:
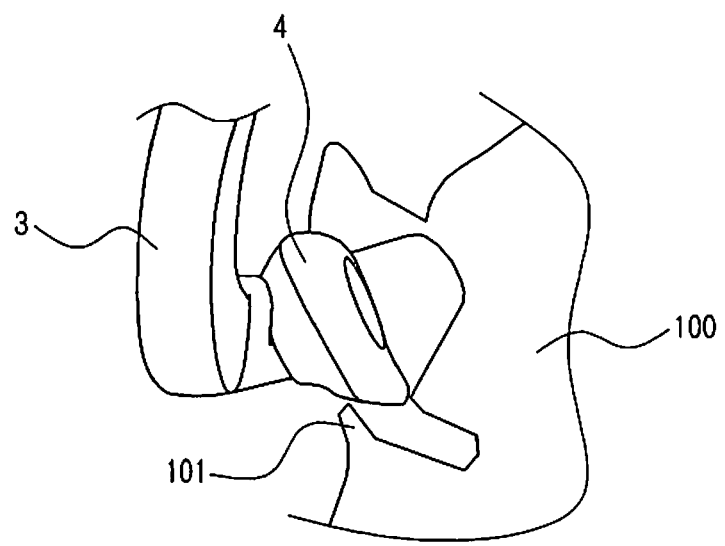
FIG. 2 is a side cross-sectional view showing a state where the earphone device shown in FIG. 1 is used.

Hereinafter, exemplary embodiments of the present invention will be described in detail with reference to the accompanying drawings. In the following description, detailed descriptions of known functions and configurations have been omitted for clarity and conciseness. Therefore, it should be apparent to those skilled in the art that various changes and modifications of the embodiments described herein can be made without departing from the scope and spirit of the invention.

As shown in FIGS. 3 through 11, an earphone device 10 having a biological information measuring apparatus includes a speaker portion 11, a sensor housing 12, a shaft 13, a support housing 14, and a stopper portion 15.

Figure 3:
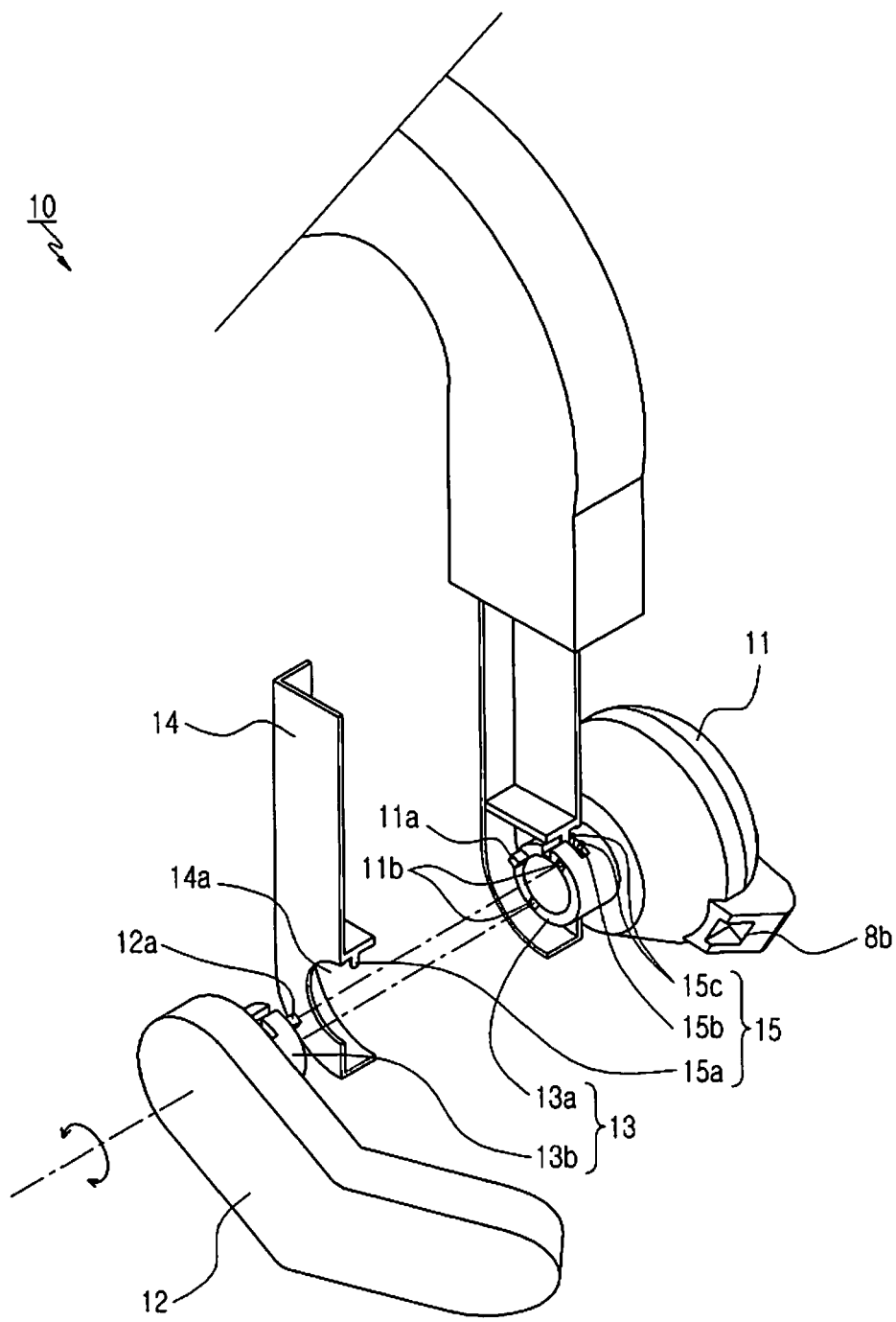
FIG. 3 is an exploded perspective view of an earphone device having a biological information measuring apparatus according to a first embodiment of the present invention.
Figure 4:
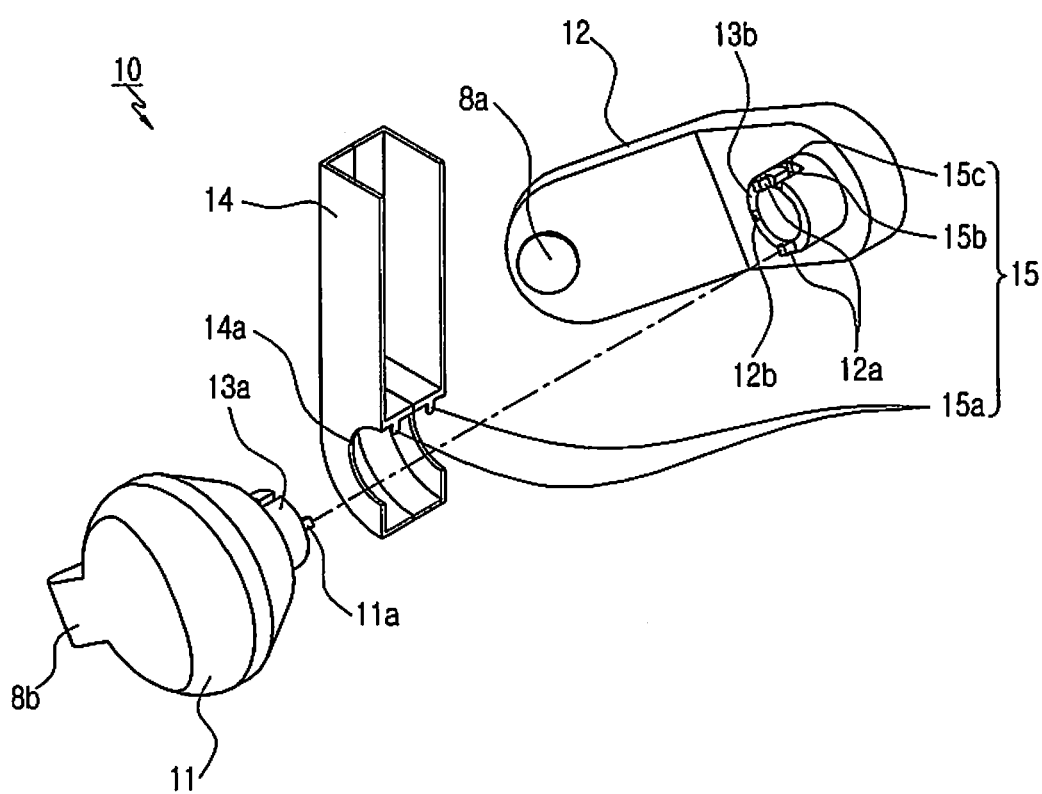
FIG. 4 is another exploded view of the earphone device having the biological information measuring apparatus according to the first embodiment of the present invention.

As shown in FIGS. 3 and 4, the biological information measuring apparatus includes a sensor unit 8 which may be referred to as a photoplethysmography (PPG) measurement sensor or a transmissive type sensor used to acquire a pulse rate that serves as base data for measuring an exercise state and an exercise quantity, and measuring and releasing stress. The sensor unit 8 may include a light emitting diode (LED) 8a and a photodiode (PD) 8b. The speaker portion 11 is provided with the PD 8b to contact a side opposite to a tragus 101 of a user's ear 100.

As shown in FIGS. 3 through 11, the sensor housing 12 is provided with the LED 8a to contact the tragus 101 of the user's ear 100, and is rotatably coupled with the speaker portion 11. The shaft 13 is provided in the speaker portion 11 and the sensor housing 12 such that the speaker portion 11 and the sensor housing 12 are coupled to rotate together. The support housing 14 is through-coupled with the shaft 13 and is provided between the speaker portion 11 and the sensor housing 12 to support rotation of the speaker portion 11 and the sensor housing 12. The stopper portion 15 is provided between the shaft 13 and the support housing 14, so that the stopper portion 15 rotates the speaker portion 11 and the sensor housing 12 in a direction for facilitating insertion into the user's ear 100 and then stops the speaker portion 11 and the sensor housing 12, and in this state, the speaker portion 11 is inserted into the user's ear 100, after which the stopper portion 15 again rotates and then stops the speaker portion 11 to urge the speaker portion 11 to contact the user's ear 100.

As shown in FIGS. 3 and 4, the shaft 13 includes a first shaft 13a and a second shaft 13b. The first shaft 13a is formed in the speaker portion 11 to be coupled with the second shaft 13b, and the second shaft 13b is formed in the sensor housing 12 to be coupled with the first shaft 13a and to rotate the speaker portion 11 and the sensor housing 12 together.

As shown in FIGS. 3 and 4, to couple the speaker portion 11 and the sensor housing 12 in a way to rotate them together, at least one or more of coupling protrusion 11a and groove 11b are formed in the first shaft 13a and at least one or more of coupling protrusion 12a and groove 12b are formed in the second shaft 13b. In the support housing 14 is formed a rotation hole 14a to pass the first shaft 13a and the second shaft 13b therethrough and support rotation.

Figure 11:
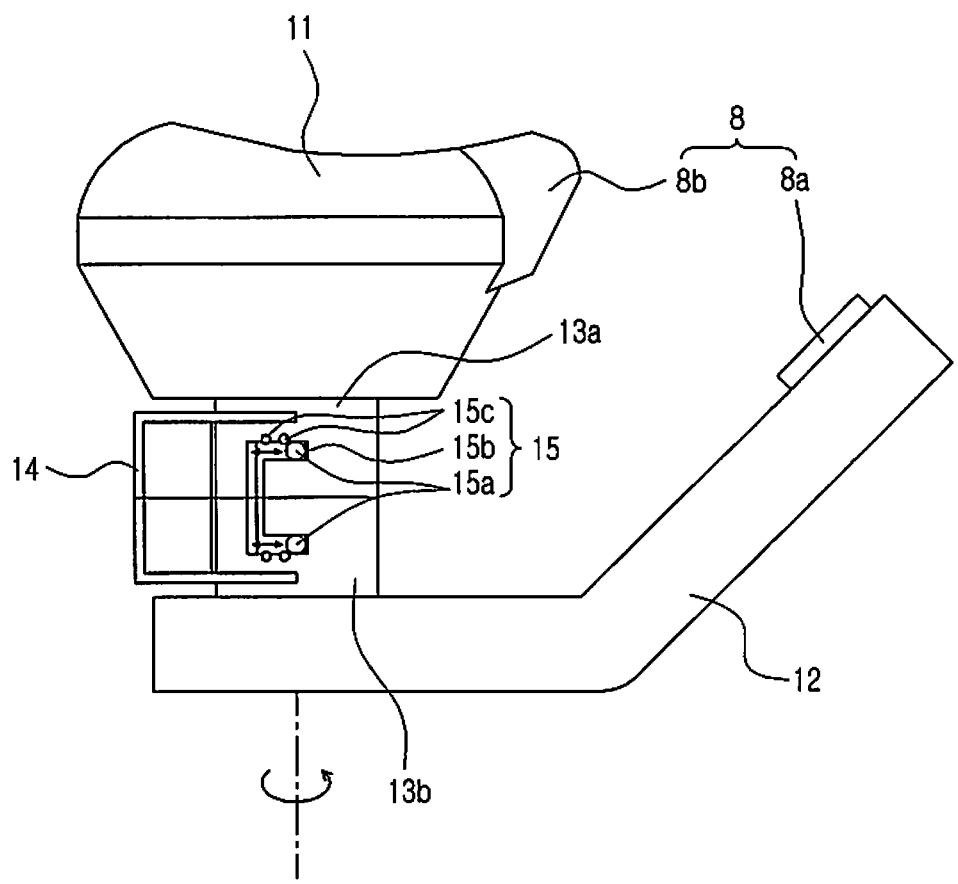
FIG. 11 is a plan view showing the in-operation state of the earphone device having the biological information measuring apparatus according to the first embodiment of the present invention.

As shown in FIGS. 3 and 11, the stopper portion 15 includes a guide pin 15a, a guide portion 15b, and at least one or more stopper engaging/disengaging portion 15c. The guide pin 15a is formed on the rotation hole 14a to be guided by the guide portion 15b. The guide portion 15b is formed in the first shaft 13a and second shaft 13b to be coupled with the guide pin 15a and to guide the guide pin 15a when the speaker portion 11 and the sensor housing 12 rotate together. The stopper engaging/disengaging portion 15c is provided in a rotation end position of the speaker portion 11 and the sensor housing 12, and is formed in the guide portion 15b such that the stopper engaging/disengaging portion 15c is engaged with or disengaged from the guide pin 15a in the rotation end position of the speaker portion 11 and the sensor housing 12 to stop the speaker portion 11 and the sensor housing 12 after their rotation.

Figure 6:
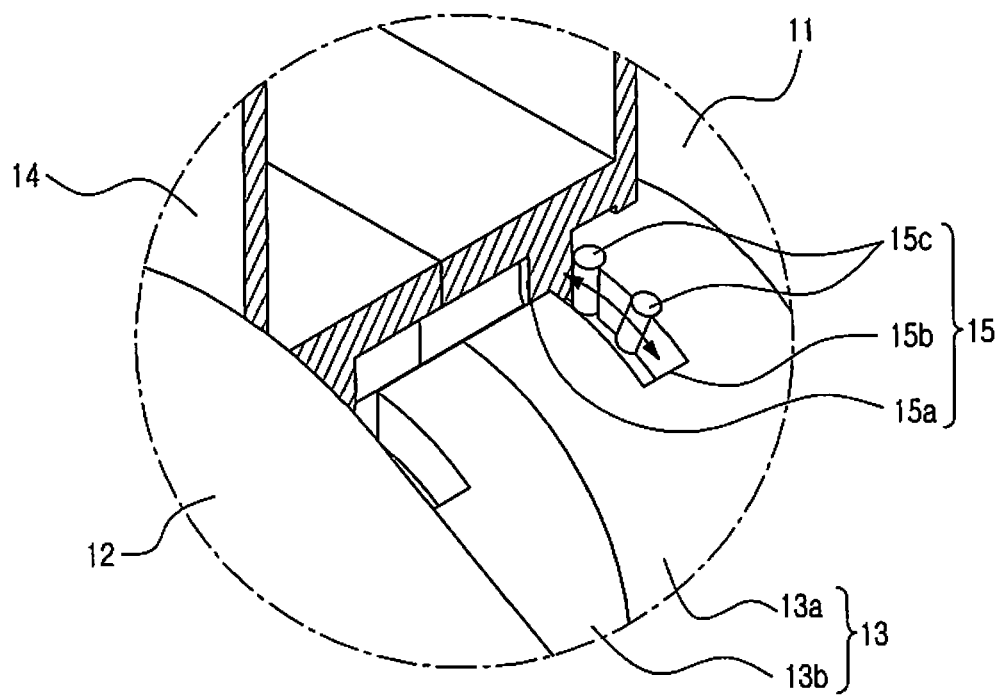
FIG. 6 is an enlarged perspective view of a portion A of FIG. 5.

As shown in FIG. 6, the guide portion 15b is a guide groove and the stopper engaging/disengaging portion 15c is a hemispheric protrusion.

With reference to FIGS. 3 through 11, a detailed description will now be made of an operation of the earphone device having the biological information measuring apparatus according to the first embodiment of the present invention.

As shown in FIGS. 3 through 11, the earphone device 10 having the biological information measuring apparatus includes the speaker portion 11 having the PD 8b, the sensor housing 12 having the LED 8a, the shaft 13, the support housing 14, and the stopper portion 15.

In the speaker portion 11 is formed the first shaft 13a where at least one or more coupling protrusion 11a and groove 11b are formed. In the sensor housing 12 is formed the second shaft 13b where at least one or more coupling protrusions 12a and groove 12b are formed.

As shown in FIGS. 3 and 4, the first shaft 13a of the speaker portion 11 and the second shaft 13b of the sensor housing 12 are coupled with each other while facing each other, and at the same time, the coupling protrusions 11a and 12b and grooves 11b and 12b formed in the first shaft 13a and the second shaft 13b are coupled with each other, respectively.

As the first shaft 13a and the second shaft 13b are coupled with each other, the speaker portion 11 and the sensor housing 12 can rotate together.

In this state, the guide portion 15b formed in the first shaft 13a and a second shaft 13b is coupled to the guide pin 15a formed in the rotation hole 14a of the support housing 14, so that the guide portion 15b can guide the guide pin 15a.

Figure 5:
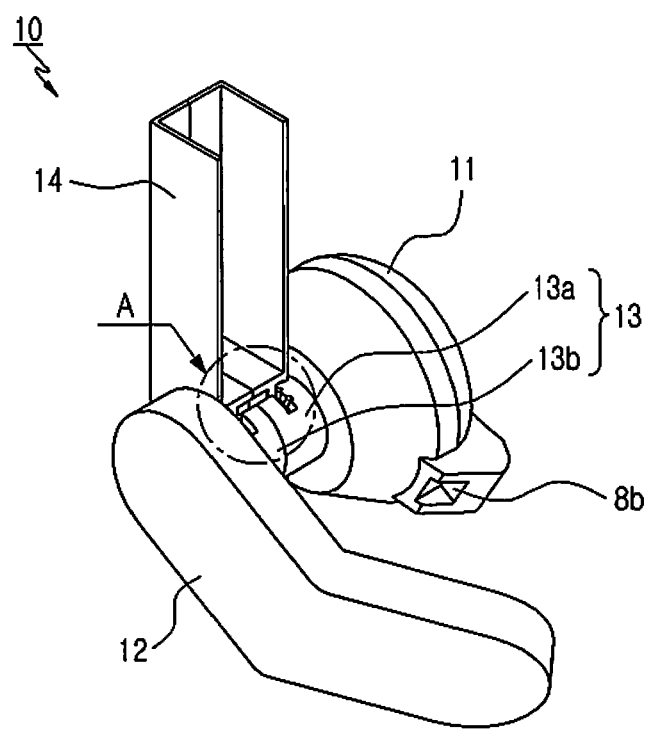
FIG. 5 is a perspective view showing an assembled state of the earphone device having the biological information measuring apparatus according to the first embodiment of the present invention.

As shown in FIGS. 5 and 6, a user rotates the speaker portion 11 and the sensor housing 12 in a normal direction, which is a direction for facilitating insertion of the speaker portion 11 into the user's ear 100 before the insertion. As the speaker portion 11 and the sensor housing 12 rotate together, the guide portion 15b of the stopper portion 15 also rotates in the normal direction. The guide portion 15b guides the guide pin 15a along with its rotation in the normal direction. The guide portion 15b is stopped by the guide pin 15a in the rotation end position of the speaker portion 11 and the sensor housing 12.

Figure 8:
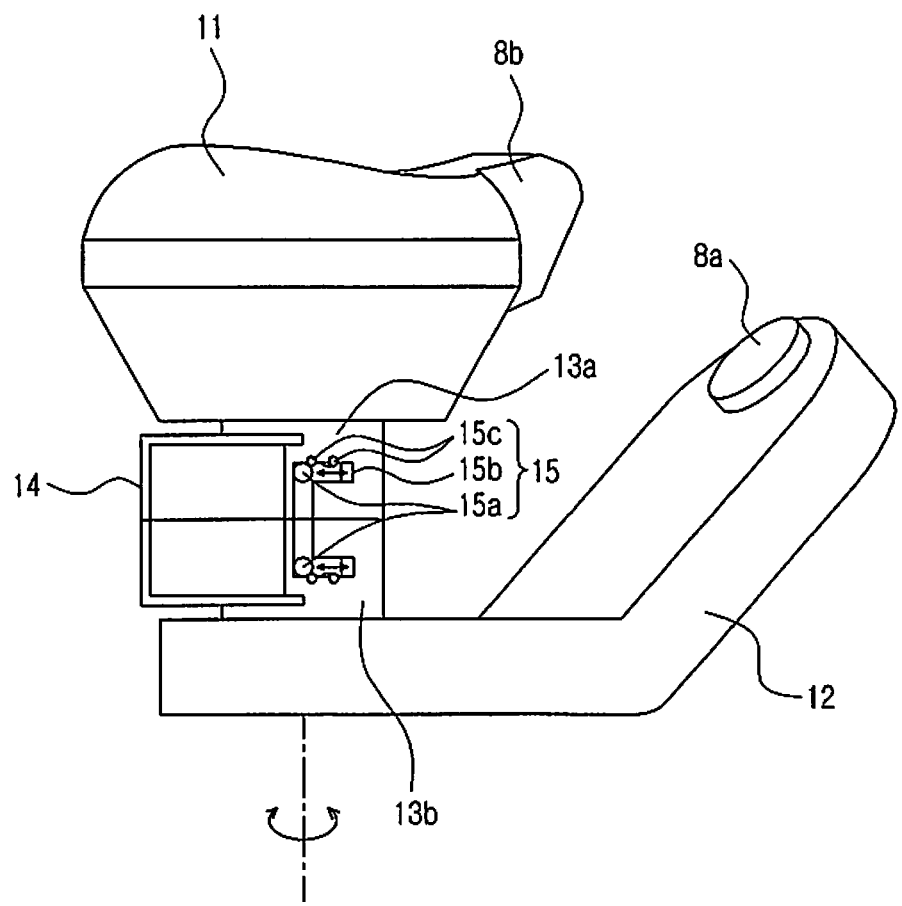
FIG. 8 is a plan view showing the pre-operation state of the earphone device having the biological information measuring apparatus according to the first embodiment of the present invention.

As shown in FIG. 8, the guide pin 15a contacts and is inserted into the stopper engaging/disengaging portion 15c formed in the rotation end position of the guide portion 15b, thus stopping the rotation of the guide portion 15b.

The guide portion 15b and the stopper engaging/disengaging portion 15c rotate the speaker portion 11 and the sensor housing 12 together in the normal direction and then stop the speaker portion 11 and the sensor housing 12.

Figure 7:
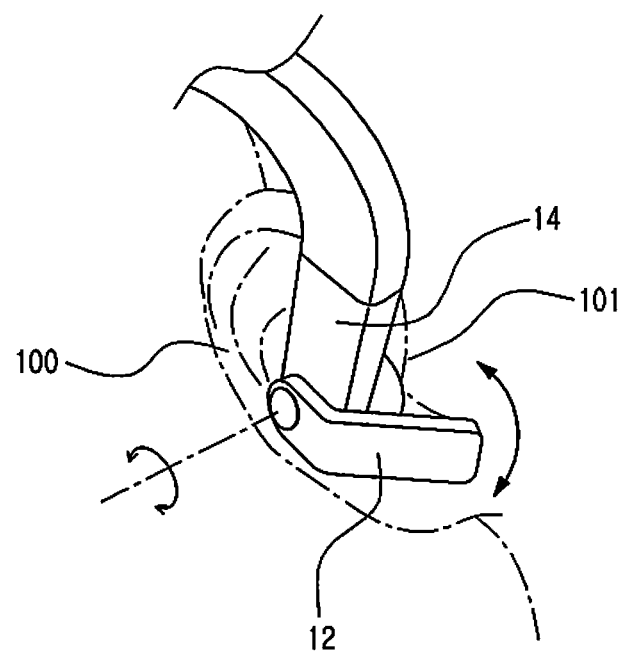
FIG. 7 is a perspective view showing a pre-operation (or before-operation) state of the earphone device having the biological information measuring apparatus according to the first embodiment of the present invention.

In this state, as shown in FIG. 7, the speaker portion 11 can be easily inserted into the user's ear 100. At this point, the PD 8b of the speaker portion 11 is positioned between intertragic notches of the ear of the user such that the speaker portion 11 is inserted into the ear 100 without being obstructed by the tragus 101 of the ear.

Figure 9:
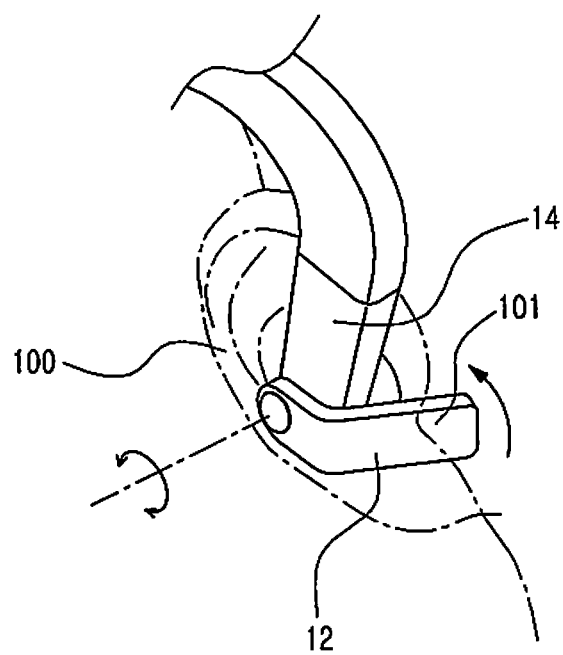
FIG. 9 is a perspective view showing a state where the earphone device having the biological information measuring apparatus according to the first embodiment of the present invention is worn on a user's ear.
Figure 10:
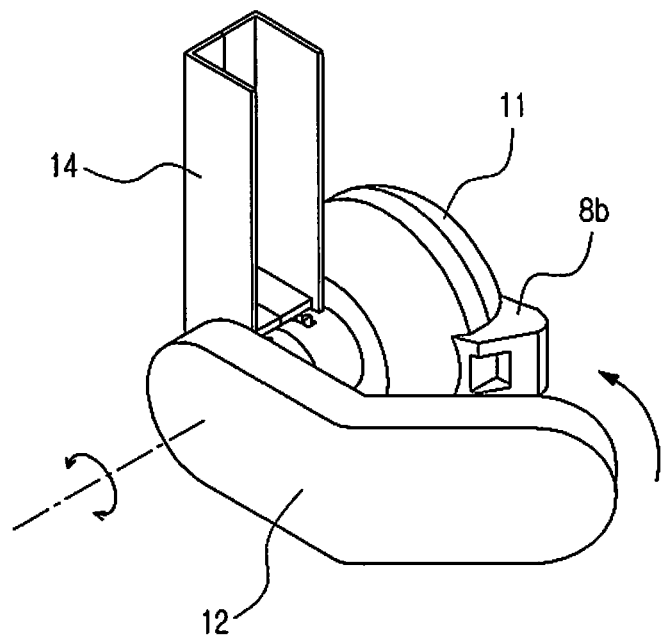
FIG. 10 is a perspective view showing an in-operation state of the earphone device having the biological information measuring apparatus according to the first embodiment of the present invention.

In this condition, as shown in FIGS. 9 through 11, after inserting the speaker portion 11, the user rotates the sensor housing 12 in a reverse direction, such that the sensor housing 12 and the speaker portion 11 rotate together in the reverse direction and the guide portion 15b also rotates.

At this point, as shown in FIG. 11, the guide pin 15a leaves the stopper engaging/disengaging portion 15c and is guided along the rotating guide portion 15b, and then stops by being inserted into another guide engaging/disengaging portion 15c formed in the rotation end position of the speaker portion 11 and the sensor housing 12.

As shown in FIG. 11, the guide portion 15b and the stopper engaging/disengaging portion 15c rotate the speaker portion 11 and the sensor housing 12 in the reverse direction and then stop the speaker portion 11 and the sensor housing 12.

At this time, as shown in FIG. 9, the sensor housing 12 contacts the tragus 101 of the ear and the LED 8a of the sensor housing 12 and the PD 8b of the speaker portion 11 face each other with the tragus 101 therebetween. In this state, the sensor unit 8 can measure the user's biological information.

With reference to FIGS. 12 through 16, a detailed description will now be made of an operation of an earphone device having the biological information measuring apparatus according to a second embodiment of the present invention.

As shown in FIGS. 12 through 16, the earphone device 10 having the biological information measuring apparatus includes the speaker portion 11 having the PD 8b, the sensor housing 12 having the LED 8a, the shaft 13, the support housing 14, the stopper portion 15, and an elastic portion 20.

In the speaker portion 11 is formed the first shaft 13a where at least one or more of coupling protrusion 11a and groove 11b are formed. In the sensor housing 12 is formed the second shaft 13b where at least one or more of coupling protrusion 12a and groove 12b are formed.

The first shaft 13a of the speaker portion 11 and the second shaft 13b of the sensor housing 12 are coupled with each other while facing each other, and at the same time, the coupling protrusions 11a and 12a and grooves 11b and 12b formed in the first shaft 13a and the second shaft 13b are also coupled with each other, respectively.

As the first shaft 13a and the second shaft 13b are coupled with each other, the speaker portion 11 and the sensor housing 12 can rotate together.

In this state, the guide portion 15b formed in the first shaft 13a and the second shaft 13b is coupled to the guide pin 15a formed in the rotation hole 14a of the support housing 14, so that the guide portion 15b can guide the guide pin 15a.

Figure 12:
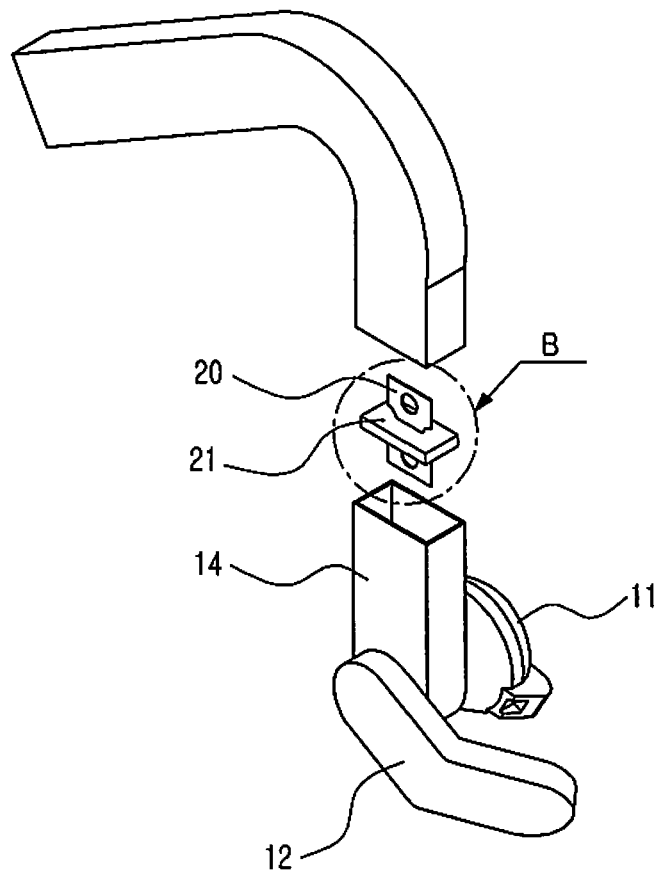
FIG. 12 is an exploded perspective view of an earphone device having a biological information measuring apparatus according to a second embodiment of the present invention.
Figure 13:
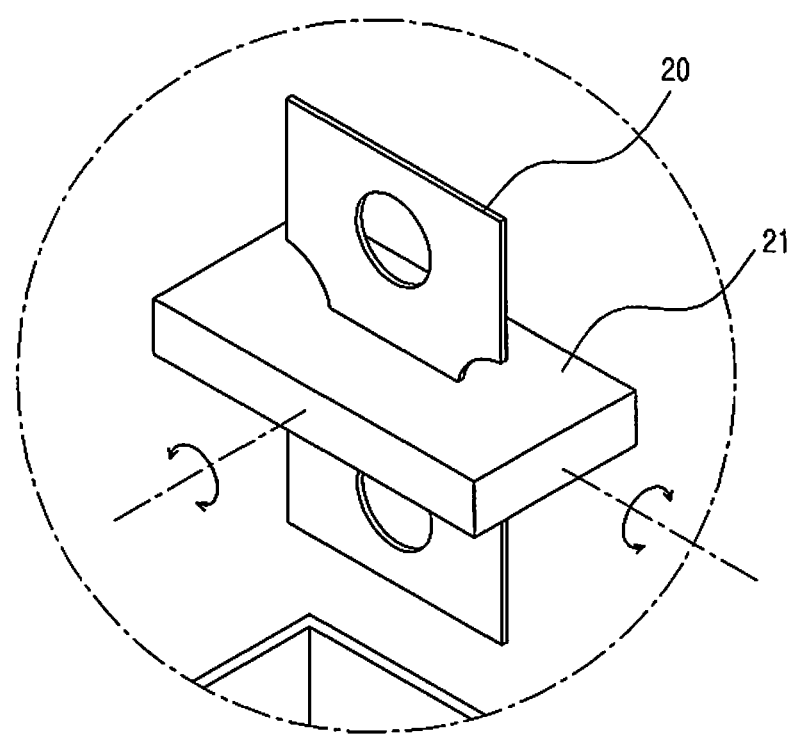
FIG. 13 is an enlarged exploded perspective view of a portion B of FIG. 12.

As shown in FIGS. 12 and 13, the elastic portion 20 is provided in the support housing 14 to absorb a force, such as inertial forces generated by external movement (for example, a user's strenuous exercise).

Figure 14:
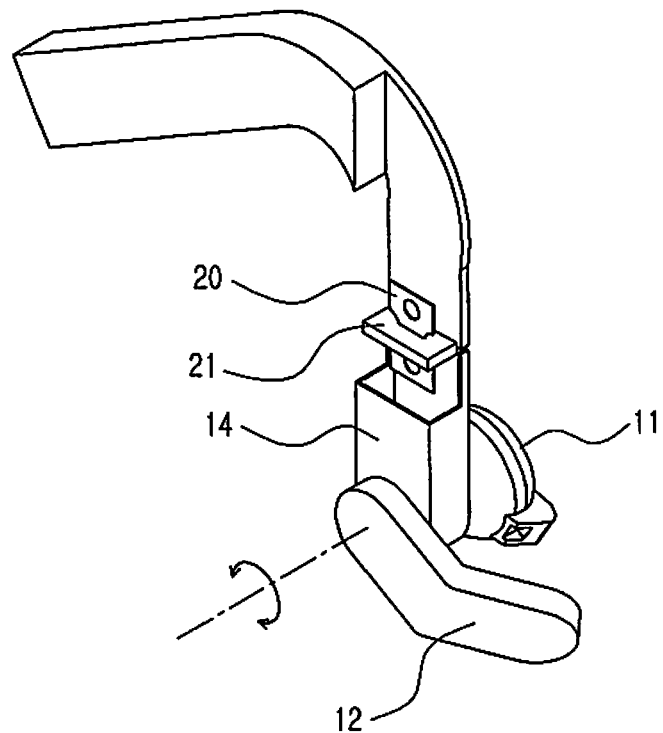
FIG. 14 is a perspective view showing an assembled state of the earphone device having the biological information measuring apparatus according to the second embodiment of the present invention.
Figure 15:
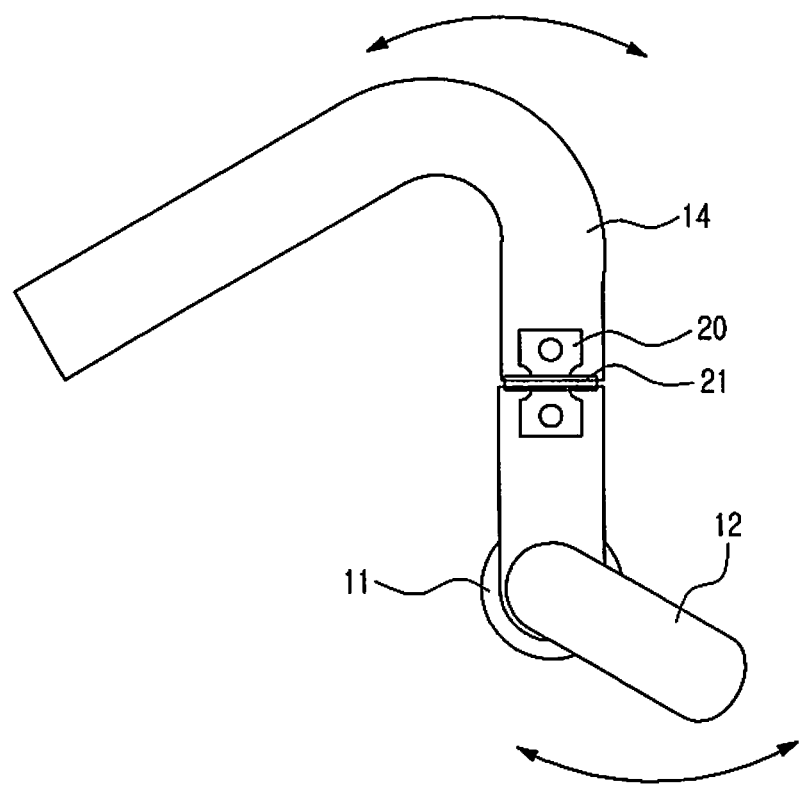
FIG. 15 is a side view showing an in-operation state of the earphone device having the biological information measuring apparatus according to the second embodiment of the present invention.
Figure 16:
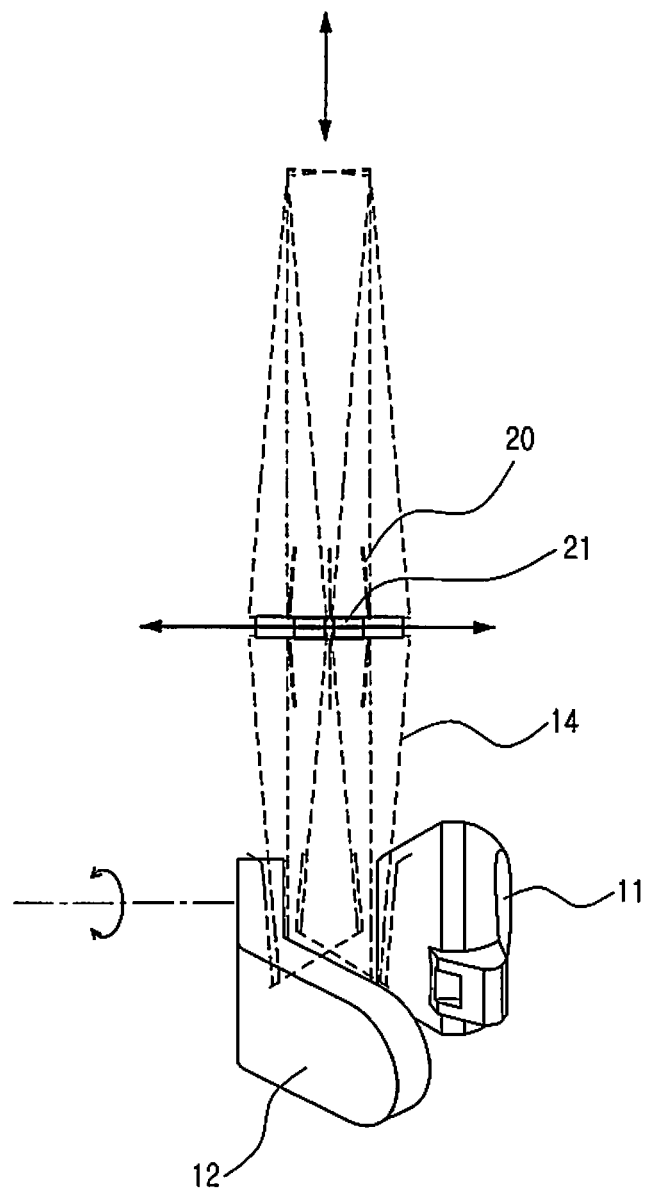
FIG. 16 is a front view showing the in-operation state of the earphone device having the biological information measuring apparatus according to the second embodiment of the present invention.

As shown in FIGS. 14 through 16, the elastic portion 20 reduces stiffness in a direction that inertial forces are delivered and increases stiffness in other directions that inertial force is not delivered. As such, the elastic portion 20 increases elasticity in a direction that large inertial forces are generated, and decreases elasticity in a direction that small inertial forces are generated. The elastic portion 20 may be composed of an elastic material, such as a metal elastic material or a leaf spring, as well as a hyper-elastic material.

As shown in FIG. 14, in the middle of the elastic portion 20 is provided a support member 21 for supporting the elastic portion 20 in a way to allow the elastic portion 20 to absorb inertial forces generated by external movement.

As shown in FIGS. 3 through 6, the user rotates the speaker portion 11 and the sensor housing 12 in the normal direction, which is a direction for facilitating insertion of the speaker portion 11 into the user's ear 100 before the insertion.

In this moment, the speaker portion 11 and the sensor housing 12 rotate together and the guide portion 15b of the stopper portion 15 also rotates in the normal direction.

The guide portion 15b guides the guide pin 15a along with its rotation in the normal direction.

The guide portion 15b is stopped by the guide pin 15a in the rotation end position of the speaker portion 11 and the sensor housing 12.

The guide pin 15a contacts and is inserted into the stopper engaging/disengaging portion 15c formed in the rotation end position of the guide portion 15b, thus stopping the rotation of the guide portion 15b.

The guide portion 15b and the stopper engaging/disengaging portion 15c rotate the speaker portion 11 and the sensor housing 12 together in the normal direction and then stop the speaker portion 11 and the sensor housing 12.

In this state, the speaker portion 11 can be easily inserted into the user's ear 100.

The PD 8b of the speaker portion 11 is positioned between intertragic notches of the user such that the speaker portion 11 is inserted into the ear 100 without being obstructed by the tragus 101 of the ear.

In this condition, as shown in FIGS. 7 and 11, after inserting the speaker portion 11, the user rotates the sensor housing 12 in a reverse direction, such that the sensor housing 12 and the speaker portion 11 rotate together in the reverse direction and the guide portion 15b also rotates.

At this point, the guide pin 15a leaves the stopper engaging/disengaging portion 15c and is guided along the rotating guide portion 15b, and then stops by being inserted into another stopper engaging/disengaging portion 15c formed in the rotation end position of the speaker portion 11 and the sensor housing 12.

The guide portion 15b and the stopper engaging/disengaging portion 15c rotate the speaker portion 11 and the sensor housing 12 in the normal direction and then stop the speaker portion 11 and the sensor housing 12.

The sensor housing 12 contacts the tragus 101 of the user's ear 100, and the LED 8a of the sensor housing 12 and the PD 8b of the speaker portion 11 face each other with the tragus 101 therebetween. In this state, the sensor unit 8 can measure biological information of the user.

As such, as shown in FIG. 7, when external movement, i.e., running or walking, occurs by the user who is wearing the earphone device 10 on the ear, a normal force applied to the sensor unit 8 perpendicular to the user's moving direction is expressed by a product of a square of a movement frequency and a mass of the earphone device 10.

As shown in FIGS. 15 and 16, the elastic portion 20 reduces inertial forces generated by the external artificial movement and reduces vibration force, by absorbing the inertial forces.

Figure 28A:
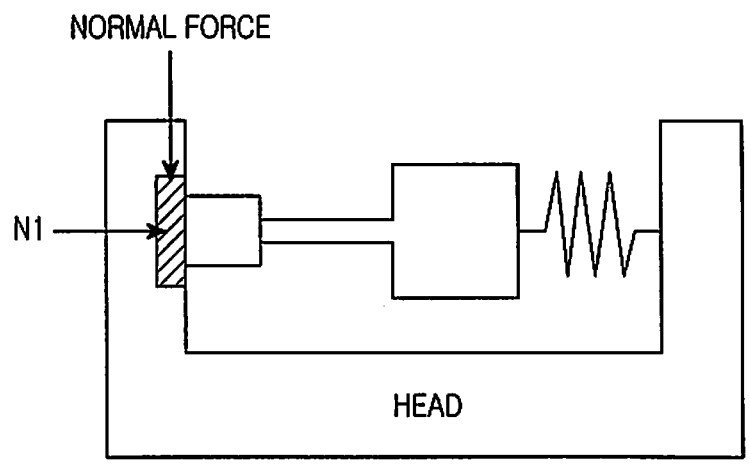
FIG. 28A is a schematic view showing a state before an elastic portion in the earphone device according to the second embodiment of the present invention or the earphone device according to the fourth embodiment of the present invention is inserted into a support housing.
Figure 28B:
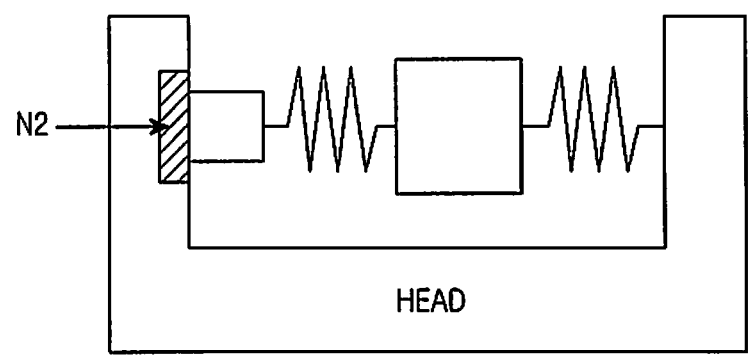
FIG. 28B is a schematic view showing a state after the elastic portion is inserted into the support housing.
Figure 28C:
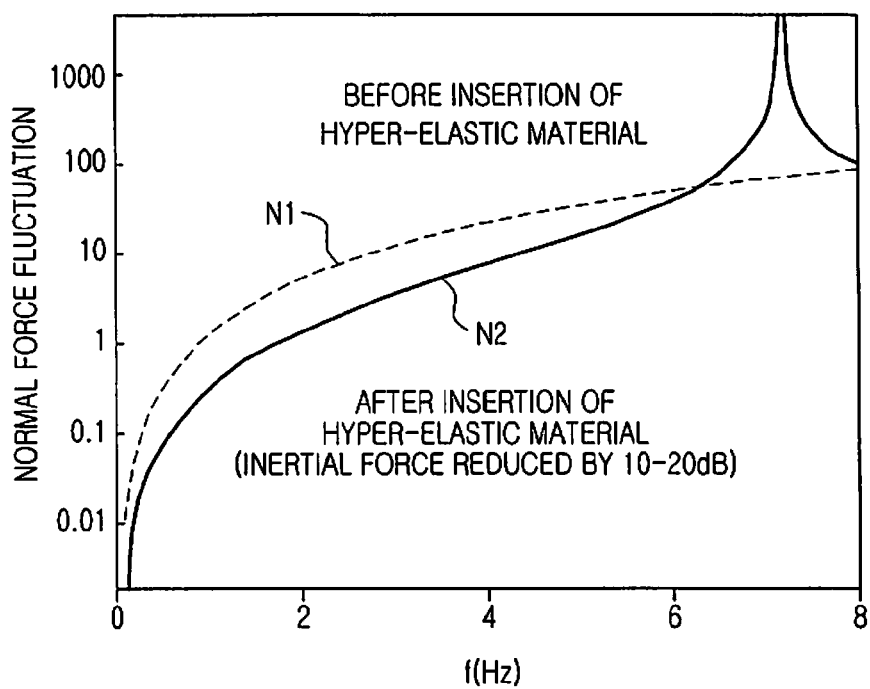
FIG. 28C is a graph showing a normal force before and after the elastic portion is inserted into the support housing.

FIGS. 28A through 28D show states before and after the elastic portion 20 is inserted into the support housing 14. As can be seen in FIG. 28C, a normal, or perpendicular, force after the insertion of the elastic portion 20 is ⅓ times less than a normal force before the insertion of the elastic portion 20, and a main frequency of external movement such as strenuous movement, e.g., running is less than 4 Hz. Based on the foregoing results, the stiffness of the elastic portion 20 which causes a resonance frequency to be higher than 4 Hz can be estimated.

Figure 28D:
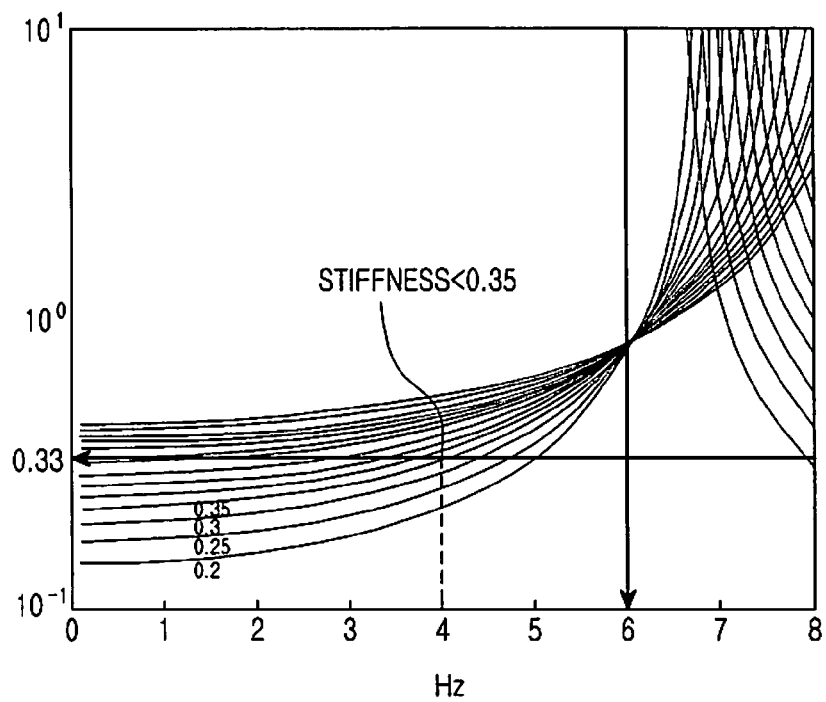
FIG. 28D is a graph showing a change in stiffness of the elastic portion.

Shown in FIG. 28D is a state of normal force for each frequency with respect to a partial stiffness. A partial stiffness by the elastic portion 20, which satisfies two avoidance conditions (including the normal force avoidance condition and the resonance frequency avoidance condition) has to be smaller than 0.35 times the opening stiffness of the support housing 14.

If the elastic portion 20 is constructed of a general elastic material, for example, a wire spring, it is not easy to reduce stiffness only perpendicular to the user's moving direction. In other words, the elastic force easily increases also in the user's moving direction, making it impossible to support the support housing 14. As a result, during insertion of the speaker portion 11, the elastic portion 20 moves down too much to enable the speaker portion 11 to be inserted.

To solve this problem, the elastic portion 20 is constructed of a hyper-elastic material.

The hyper-elastic material is preferably a nitinol material, which is transformed according to a transformation temperature at a transformation rate greater than a yield strength. The hyper-elastic nitinol material is applied with a constant force, and may be transformed at a transformation rate of up to about 8%, unlike a general elastic material.

As shown in FIGS. 15 and 16, the hyper-elastic material portion 20 is in an 'I' shape and is coupled with an elastic material such as urethane. The hyper-elastic material portion 20 has different cross-sections, that is, a cross-section in a perpendicular direction to the moving direction is different from a cross-section in the moving direction. As a result, when a load generated by opening is applied to a thin and wide cross-section like a spring-board, a pressure applied to the section easily exceeds a hyper-elastic threshold pressure and works in a hyper-elastic region.

As such, the hyper-elastic material portion 20 reduces stiffness in a direction that the inertial force is delivered, and increases stiffness in other directions that the inertial force is not delivered, thereby improving wearing comfort by reducing stiffness in a direction affecting the wearing comfort, while minimizing the inertial forces generated by external movement.

With reference to FIGS. 17 through 22, a detailed description will now be made of an operation of an earphone device having the biological information measuring apparatus according to a third embodiment of the present invention.

As shown in FIGS. 17 through 22, an earphone device 200 having the biological information measuring apparatus includes a speaker portion 201, a sensor housing 22, a gear portion 23, and a support housing 24.

Figure 22:
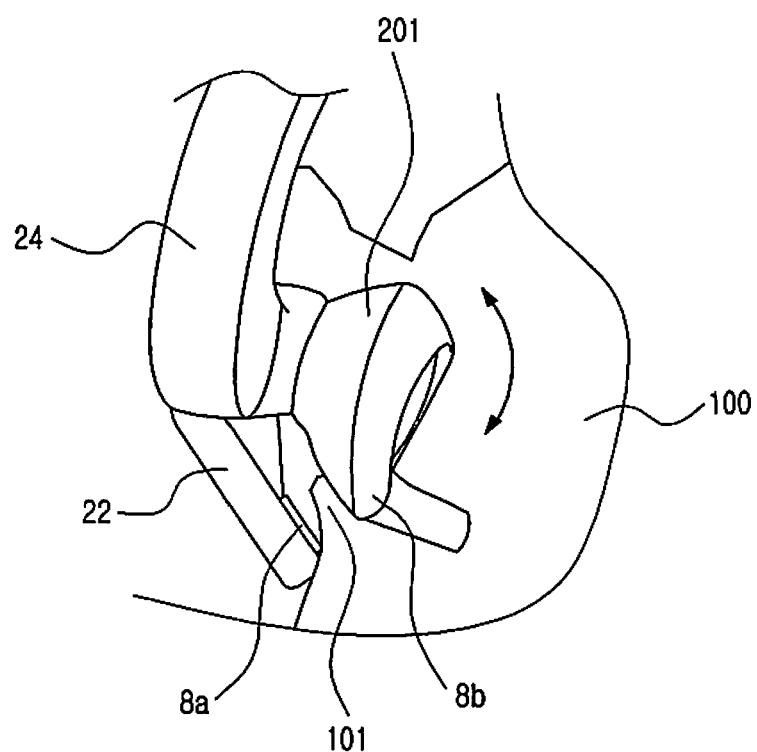
FIG. 22 is a side cross-sectional view showing a state where the earphone device having the biological information measuring apparatus according to the third embodiment of the present invention is worn on a user's ear.

As shown in FIG. 22, the speaker portion 201 includes the PD 8b to contact a side opposite to the tragus 101. The sensor housing 22 includes the LED 8a to contact the tragus 101 and is rotatably coupled with the speaker portion 201.

Figure 17:
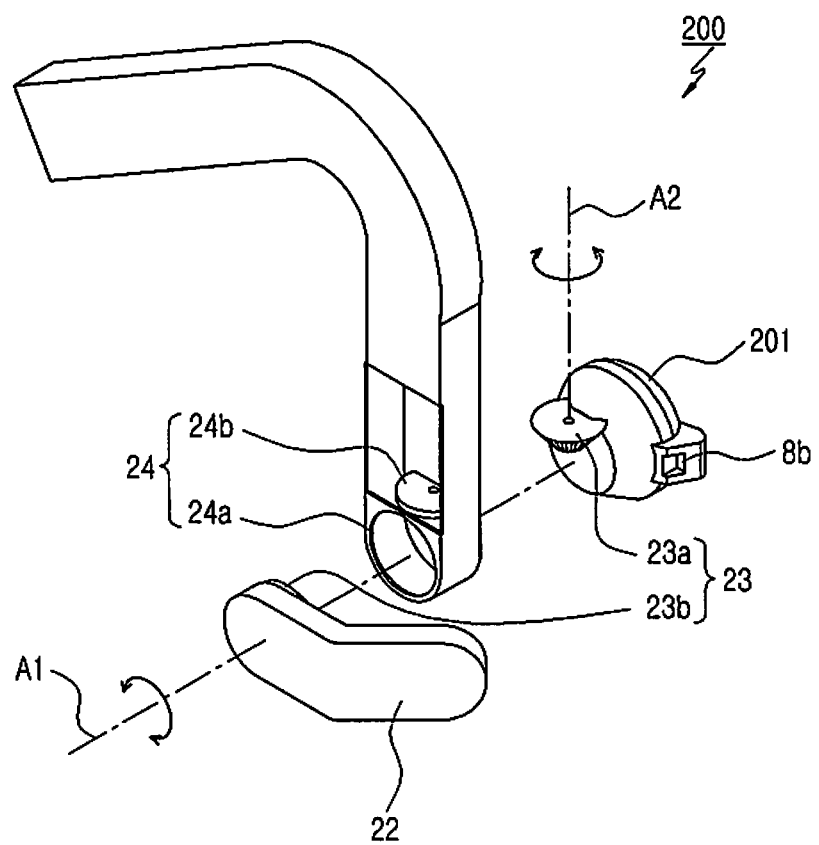
FIG. 17 is an exploded perspective view showing an earphone device having a biological information measuring apparatus according to a third embodiment of the present invention.
Figure 18:
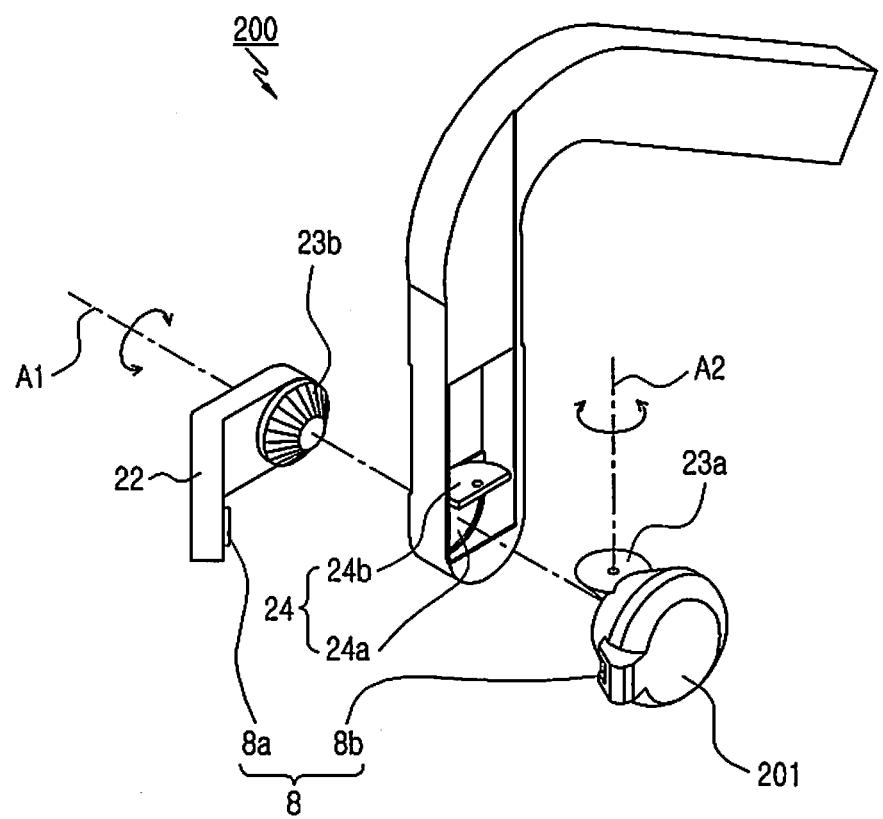
FIG. 18 is another exploded perspective view showing the earphone device having the biological information measuring apparatus according to the third embodiment of the present invention.
Figure 19:
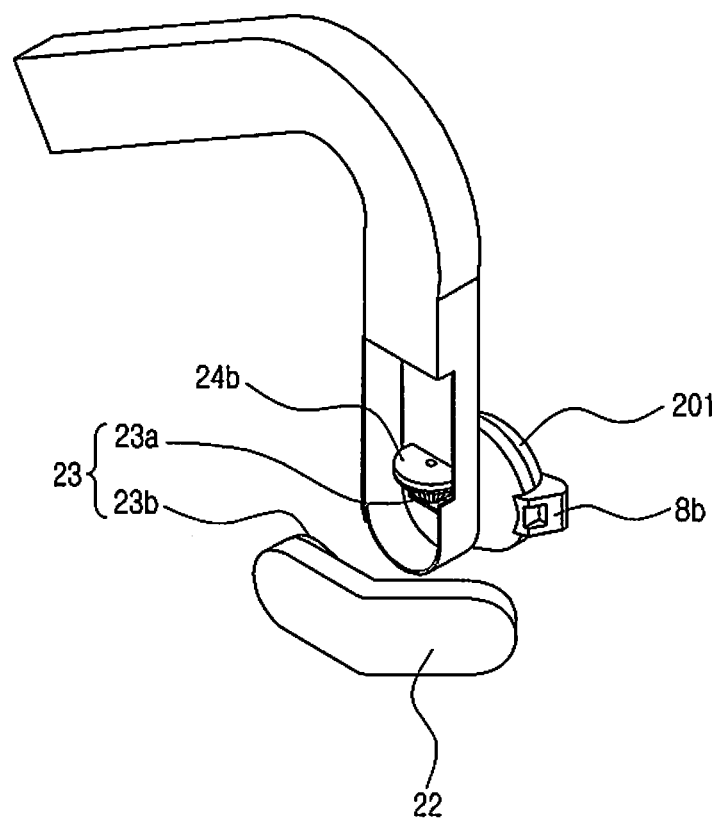
FIG. 19 is a perspective view showing a partially assembled state of the earphone device having the biological information measuring apparatus according to the third embodiment of the present invention.

As shown in FIGS. 17 through 19, the gear portion 23 is provided in the speaker portion 201 and the sensor housing 22 to rotate the sensor housing 22 about a first rotation axis A1 and rotate the speaker portion 201 about a second rotation axis A2. The support housing 24 supports the speaker portion 201 and the sensor housing 22 to allow the sensor housing 22 and the speaker portion 201 to rotate by means of the gear portion 23 about the first rotation axis A1 and the second rotation axis A2, respectively.

Figure 20:
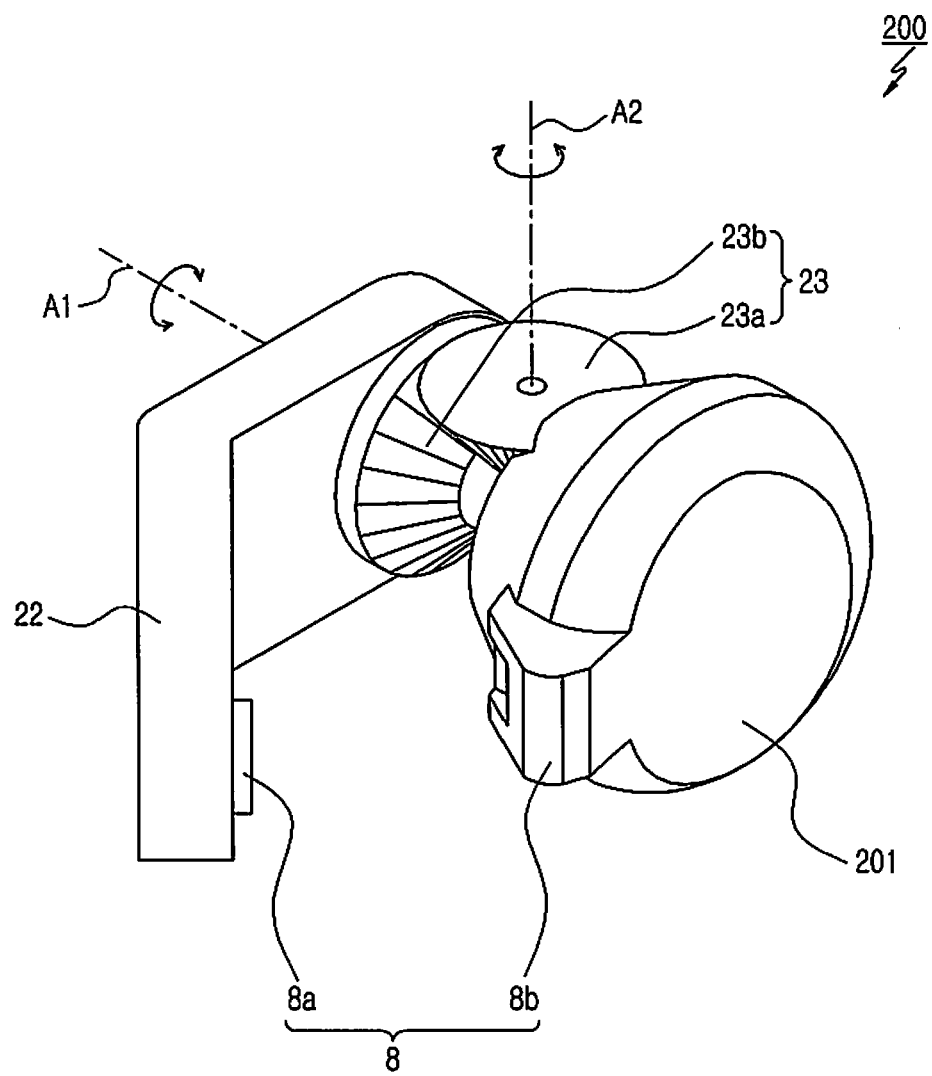
FIG. 20 is a perspective view showing a pre-operation (or before-operation) state of the earphone device having the biological information measuring apparatus according to the third embodiment of the present invention.
Figure 21:
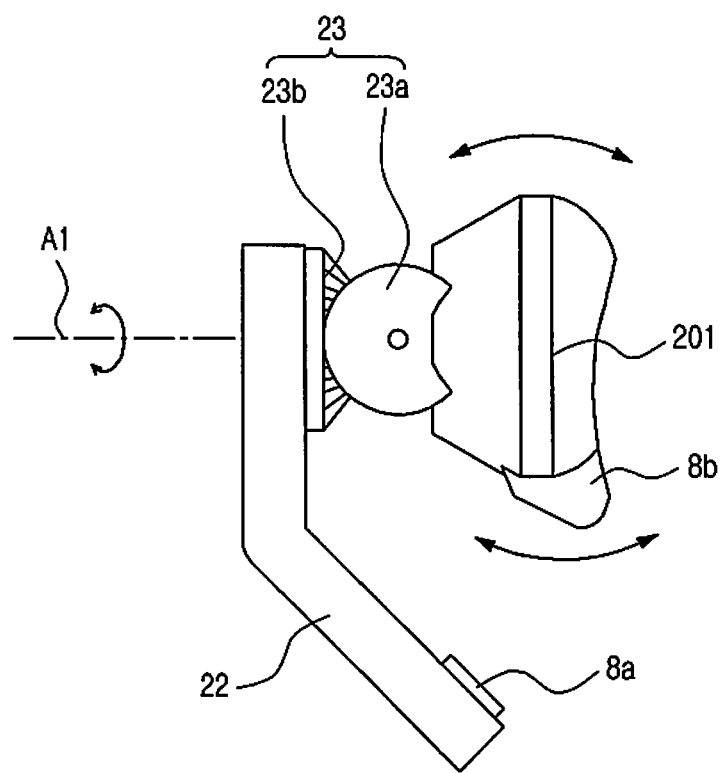
FIG. 21 is a plan view showing the pre-operation state of the earphone device having the biological information measuring apparatus according to the third embodiment of the present invention.

As shown in FIGS. 20 and 21, the gear portion 23 may be a bevel gear or a spur gear, or may be a gear other than the bevel gear or the spur gear.

In the support housing 24 is formed a first support portion 24a which supports the sensor housing 22 in a way to allow rotation of the sensor housing 22 about the first rotation axis A1. In the support housing 24 is also formed a second support portion 24b which is coupled with and supports a speaker-side gear portion 23a formed on the speaker portion 201 in a way to allow rotation of the speaker portion 201 about the second rotation axis A2.

In this state, as shown in FIG. 20, when the user first rotates the sensor housing 22 about the first axis A1 in a normal direction which is a direction for facilitating insertion of the speaker portion 201 into the user's ear 100 prior to the insertion, the sensor housing 22 and a housing-side gear portion 23b formed in the sensor housing 22 also rotate together about the first rotation axis A1 and the speaker-side gear portion 23a engaged with the housing-side gear portion 23b also rotates about the second rotation axis A2 in the normal direction. As the speaker-side gear portion 23a rotates about the second rotation axis A2, the speaker portion 201 also rotates. The sensor housing 22 rotates about the first rotation axis A1 toward a lower portion of the support housing 24, and the speaker portion 201 rotates about the second rotation axis A2 outwardly from the support housing 24. In this state, the speaker portion 201 can be easily inserted into the user's ear 100.

In this condition, the PD 8b of the speaker portion 201 is positioned between intertragic notches of the user's ear such that the speaker portion 201 is inserted into the ear 100 without being obstructed by the tragus 101 of the ear.

At this point, as shown in FIGS. 21 and 22, after inserting the speaker portion 201, the user rotates the sensor housing 22 about the first rotation axis A1 in a reverse direction and in this state, the speaker portion 201 rotates about the second rotation axis A2 in the reverse direction.

As such, the sensor housing 22 rotates about the first rotation axis A1 in the reverse direction toward an upper portion of the support housing 24 and the speaker portion 201 rotates about the second rotation axis A2 in the reverse direction inwardly from the support housing 24.

The LED 8a of the sensor housing 22 and the PD 8b of the speaker portion 201 come close to each other, contact the tragus 101, and face each other with the tragus 101 therebetween. In this state, the sensor unit 8 can measure biological information of the user.

With reference to FIGS. 23 through 27, a detailed description will now be made of an operation of an earphone device having a biological information measuring apparatus according to a fourth embodiment of the present invention.

Figure 23:
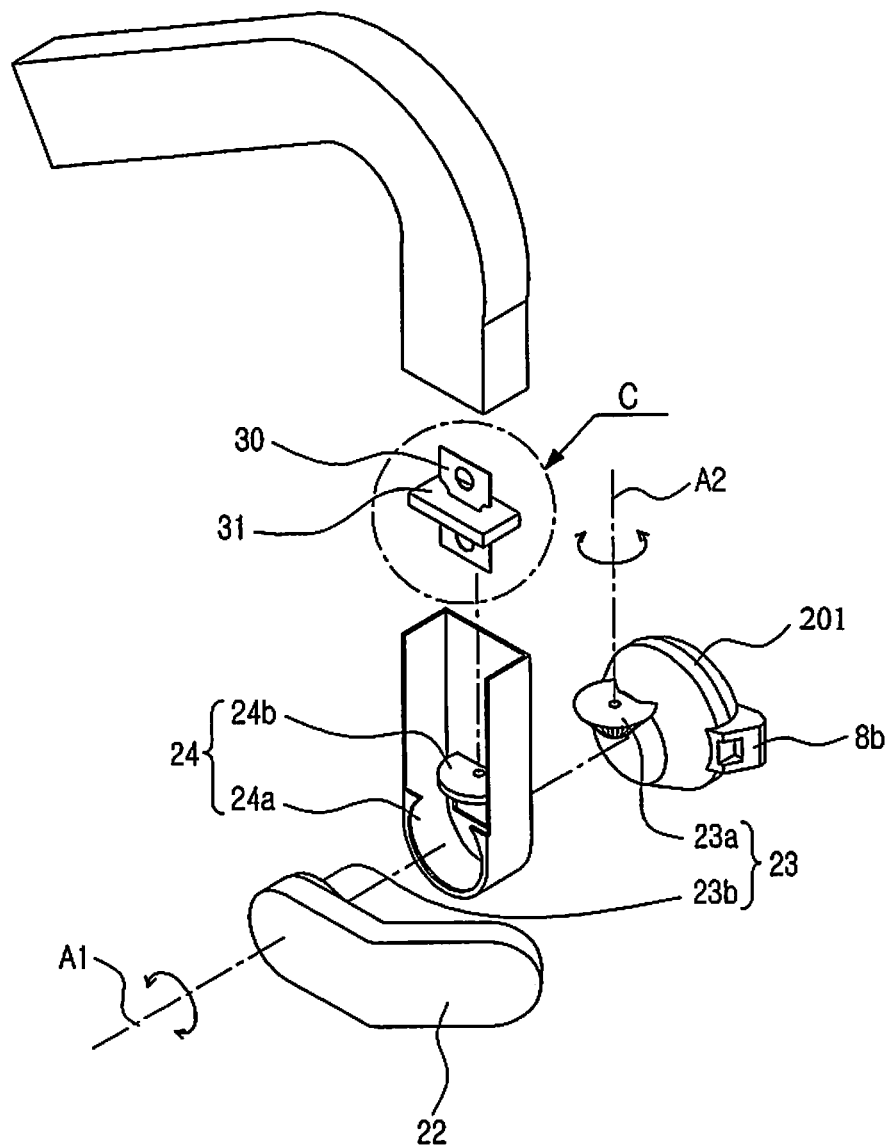
FIG. 23 is an exploded perspective view of an earphone device having a biological information measuring apparatus according to a fourth embodiment of the present invention.
Figure 24:
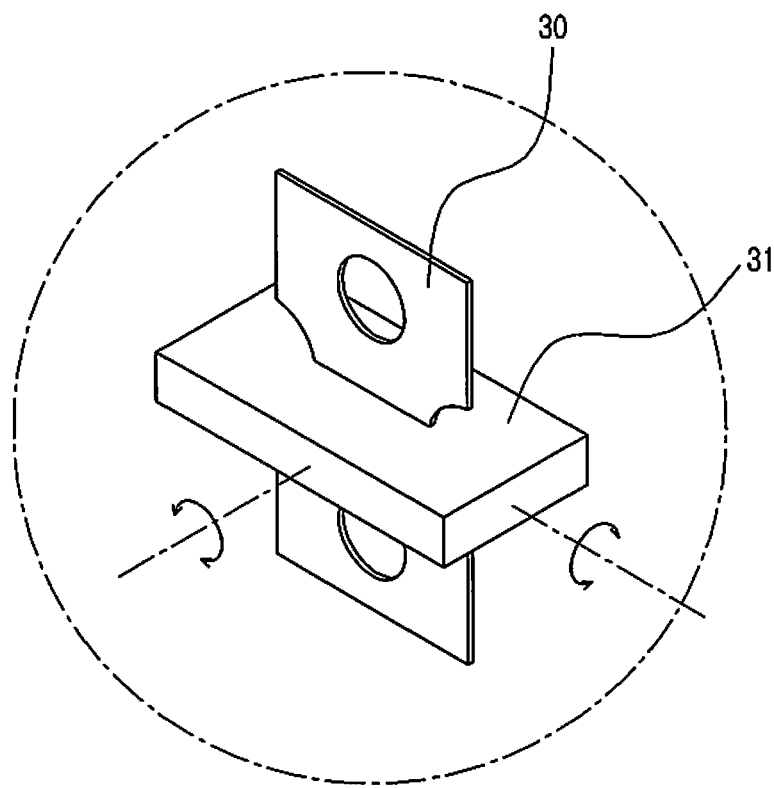
FIG. 24 is an enlarged exploded perspective view of a portion C of FIG. 23.
Figure 25:
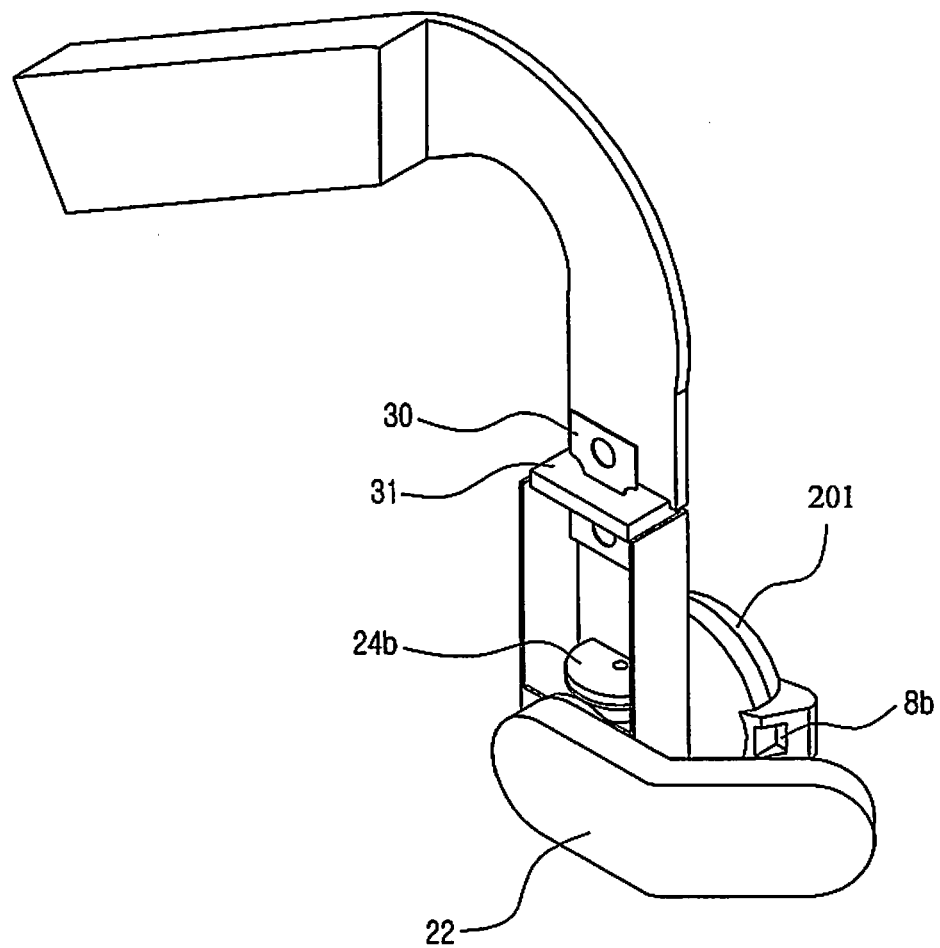
FIG. 25 is a perspective view showing an assembled state of the earphone device having the biological information measuring apparatus according to the fourth embodiment of the present invention.

As shown in FIGS. 23 and 24, an elastic portion 30 may be provided to reduce inertial forces generated by external movements and reduces vibration force, by absorbing the inertial forces.

As described above, FIGS. 28A through 28C show states before and after the elastic portion 30 is inserted into the support housing 24. As can be seen, a normal, or perpendicular, force after the insertion of the elastic portion 30 is ⅓ times less than a normal force before the insertion of the elastic portion 30, and a main frequency of external artificial movement such as strenuous movement, e.g., running is less than 4 Hz. Based on the foregoing results, the stiffness of the elastic portion 30, which causes a resonance frequency to be higher than 4 Hz can be estimated.

Shown in FIG. 28D is a state normal force for each frequency with respect to a partial stiffness. A partial stiffness by the elastic portion 30, which satisfies two avoidance conditions including the normal force avoidance condition and the resonance frequency avoidance condition, has to be smaller than 0.35 times the opening stiffness of the support housing 24.

As also described above, if the elastic portion 30 is composed of a general elastic material, for example, a wire spring, it is not easy to reduce stiffness only perpendicular to the user's moving direction. In other words, the elastic force easily increases also in the user's moving direction, making it impossible to support the support housing 24. As a result, during insertion of the speaker portion 201, the elastic portion 30 moves down too much to enable the speaker portion 201 to be inserted.

To solve this problem, the elastic portion 30 is constructed of a hyper-elastic material, such as nitinol.

Figure 26:
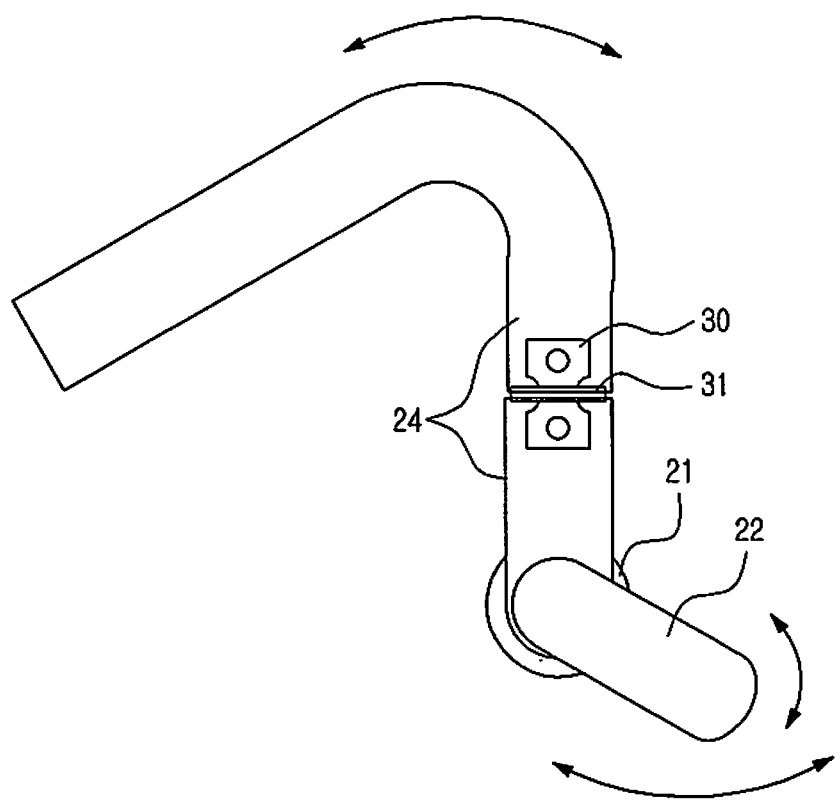
FIG. 26 is a side view showing an in-operation state of the earphone device having the biological information measuring apparatus according to the fourth embodiment of the present invention.
Figure 27:
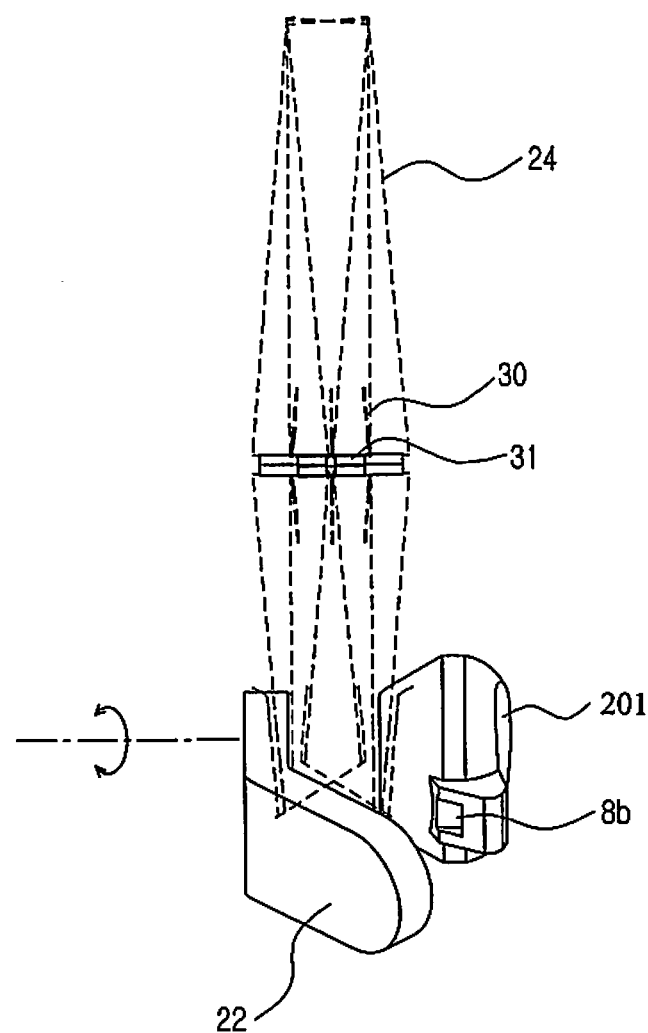
FIG. 27 is a front view showing the in-operation state of the earphone device having the biological information measuring apparatus according to the fourth embodiment of the present invention.

As shown in FIGS. 26 and 27, the hyper-elastic material 30 in an 'I' shape and is coupled with an elastic material such as urethane. The hyper-elastic material 30 has different cross-sections, that is, a cross-section in a perpendicular direction to the moving direction is different from a cross-section in the moving direction. As a result, when a load generated by opening is applied to a thin and wide cross-section like a spring-board, a pressure applied to the section easily exceeds a hyper-elastic threshold pressure and works in a hyper-elastic region.

As shown in FIG. 27, the elastic portion 30 reduces stiffness in a direction that the inertial force is delivered, and increases stiffness in other directions that the inertial force is not delivered, thereby improving wearing comfort by reducing stiffness in a direction affecting the wearing comfort, while minimizing the inertial force generated by external movement.

An earphone device having a biological information measuring apparatus according to the embodiments of the present invention has been illustrated as a representative example. However, an earphone device having a biological information measuring apparatus according to the present invention is not limited to the earphone device, and may be applied to any small-size electronic device (not shown) such as an information communication apparatus and a multimedia apparatus, which can contact a user's body.

It would be obvious to those of ordinary skill in the art that the above-described earphone device having the biological information measuring apparatus according to the present invention is not limited to the foregoing embodiments and drawings, and various substitutions, modifications, and changes may be made therein without departing from the spirit and scope of the invention.

What is claimed is:

1. An earphone device having a biological information measuring apparatus, the earphone device comprising:
  a speaker portion;
  a sensor housing rotatably coupled with the speaker portion;
  a shaft provided in the speaker portion and the sensor housing to couple the speaker portion with the sensor housing, wherein the shaft comprises a first shaft formed in the speaker portion and a second shaft formed in the sensor housing configured to be coupled with the first shaft to enable the speaker portion and the sensor housing to rotate together;
  a support housing coupled with the shaft to pass the shaft therethrough, the support housing supporting the speaker portion and the sensor housing during rotation; and a stopper portion provided in the shaft and the support housing to permit rotation of the speaker portion and the sensor housing and then to stop the rotation, thereby facilitating insertion into a user's ear and urging the speaker portion to contact the user's ear.

2. The earphone device of claim 1, wherein at least one or more coupling protrusions and grooves are formed in the first shaft and the second shaft to couple the speaker portion with the sensor housing to enable the speaker portion and the sensor housing to rotate together.

3. The earphone device of claim 1, wherein a rotation hole is formed in the support housing to pass the shaft therethrough and to support rotation.

4. The earphone device of claim 3, wherein the stopper portion comprises:
   a guide pin formed in the rotation hole;
   a guide portion formed in the shaft and coupled with the guide pin to guide the guide pin during rotation of the speaker portion and the sensor housing; and
   at least one or more stopper engaging/disengaging portions formed in the guide portion, provided in a rotation end position of the speaker and the sensor housing, and engaged with or disengaged from the guide pin in the rotation end position of the speaker portion and the sensor housing to stop the speaker portion and the sensor housing after rotation of the speaker portion and the sensor housing.

5. The earphone device of claim 3, wherein the stopper portion permits rotation of the speaker portion and the sensor housing in a direction for facilitating insertion into the user's ear and then stops the rotation of the speaker portion and the sensor housing before the insertion, and permits rotation of the speaker portion and the sensor housing in a reverse direction and then stops the rotation of the speaker portion and the sensor housing after the insertion, thereby urging the speaker portion to contact the user's ear.

6. An earphone device having a biological information measuring apparatus, the earphone device comprising:
   a speaker portion;
   a sensor housing rotatably coupled with the speaker portion;
   a shaft provided in the speaker portion and the sensor housing to couple the speaker portion with the sensor housing, wherein the shaft comprises a first shaft formed in the speaker portion and a second shaft formed in the sensor housing configured to be coupled with the first shaft to enable the speaker portion and the sensor housing to rotate together;
   a support housing coupled with the shaft to pass the shaft therethrough, the support housing supporting the speaker portion and the sensor housing during rotation;
   a stopper portion provided in the shaft and the support housing to permit rotation of the speaker portion and the sensor housing and then to stop the rotation, thereby facilitating insertion into a user's ear and urging the speaker portion to contact the user's ear; and
   an elastic portion provided in the support housing to absorb inertial forces generated by external movement.

7. The earphone device of claim 6, wherein the elastic portion reduces stiffness in a direction that the inertial force is delivered, and increases stiffness in other directions that the inertial force is not delivered.

8. The earphone device of claim 6, wherein the elastic portion comprises a hyper-elastic material, which includes a support member for supporting the elastic portion to allow the elastic portion to absorb the inertial force.

9. The earphone device of claim 8, wherein the elastic portion is in an 'I' shape.

10. An earphone device having a biological information measuring apparatus, the earphone device comprising:
    a speaker portion;
    a sensor housing rotatably coupled with the speaker portion;
    a gear portion provided in the speaker portion and the sensor housing to enable rotation of the sensor housing about a first rotation axis and the speaker portion about a second rotation axis; and
    a support housing for supporting the speaker portion and the sensor housing to enable the speaker portion and the sensor housing to rotate about the second rotation axis and the first rotation axis by means of the gear portion,
    wherein the gear portion is configured to enable the speaker portion and the sensor housing to rotate together.

11. The earphone device of claim 10, wherein the gear portion comprises one of a bevel gear or a spur gear.

12. The earphone device of claim 10, wherein a first support portion is formed in the support housing and supports the sensor housing to allow the sensor housing to rotate about the first rotation axis, and
    wherein a second support portion is formed in the support housing and is coupled with and supports a speaker-side gear portion formed on the speaker portion to allow the speaker portion to rotate about the second rotation axis.

13. An earphone device having a biological information measuring apparatus, the earphone device comprising:
    a speaker portion;
    a sensor housing rotatably coupled with the speaker portion;
    a gear portion provided in the speaker portion and the sensor housing to enable rotation of the sensor housing about a first rotation axis and the speaker portion about a second rotation axis;
    a support housing for supporting the speaker portion and the sensor housing to allow the speaker portion and the sensor housing to rotate about the second rotation axis and the first rotation axis by means of the gear portion; and
    an elastic portion provided in the support housing to absorb inertial forces generated by external movement,
    wherein the gear portion is configured to enable the speaker portion and the sensor housing to rotate together.

14. The earphone device of claim 13, wherein the elastic portion reduces stiffness in a direction that the inertial force is delivered, and increases stiffness in other directions that the inertial force is not delivered.

15. The earphone device of claim 13, wherein the elastic portion comprises a hyper-elastic material, which includes a support member for supporting the elastic portion to allow the elastic portion to absorb the inertial force.

16. The earphone device of claim 15, wherein the elastic portion is in an 'I' shape.

* * * * *